United States Patent [19]

Loh et al.

[11] Patent Number: 4,828,601

[45] Date of Patent: May 9, 1989

[54] CHEMICAL TOBACCO SUCKER CONTROL

[75] Inventors: William Loh, Petaluma; Pawan K. Bassi, Benicia, both of Calif.

[73] Assignee: Chevron Research Company, San Francisco, Calif.

[21] Appl. No.: 101,324

[22] Filed: Sep. 25, 1987

[51] Int. Cl.⁴ ............................................. A01N 43/18
[52] U.S. Cl. ............................................ 71/78; 71/90; 549/13
[58] Field of Search .................. 71/78, 90; 549/13

[56] References Cited

U.S. PATENT DOCUMENTS

| | | | |
|---|---|---|---|
| 4,432,786 | 2/1984 | Loh | 71/90 |
| 4,440,566 | 4/1984 | Luo | 71/98 |
| 4,596,877 | 6/1986 | Becker et al. | 549/13 |
| 4,624,696 | 11/1986 | Keil et al. | 71/88 |
| 4,701,205 | 10/1987 | Omid et al. | 71/78 |

*Primary Examiner*—Glennon H. Hollrah
*Assistant Examiner*—A. A. Owens
*Attorney, Agent, or Firm*—S. R. La Paglia; R. C. Gaffney; L. S. Squires

[57] ABSTRACT

Methods and compositions for controlling tobacco suckers, which comprise administering an effective amount of certain 2-[1-[(5-chlorothien-2-yl)methoxyimino]ethyl]-3-hydroxy or alkanoyloxy-5-(tetrahydro-2H-thiopyran-3-yl)cyclohex-2-en-1-one derivatives to said tobacco plants or their growth medium.

7 Claims, No Drawings

CHEMICAL TOBACCO SUCKER CONTROL

BACKGROUND OF THE INVENTION

This invention relates to the chemical control of tobacco suckers (i.e., axillary buds) via the application of certain 3-hydroxy and 3-alkanoyloxy-2-[1-(substituted-oxyimino)ethyl]-5-substituted-cyclohex-2-en-1-one derivatives.

Tobacco crop management requires that the terminal growing meristem be removed so that the number of usable leaves and their quality can be optimized. The removal of the terminal meristem, a process called topping, encourages the rapid development of lateral buds. These lateral buds are known as suckers. These suckers, if allowed to grow, can interfere with the proper development of usable tobacco leaves resulting in serious economic losses for the grower.

Manual removal of these suckers is very labor intensive. Chemicals are used, therefore, to arrest the development of lateral buds after topping. These chemicals mimic the phenomenon of apical dominance in tobacco cultivation after the plants are topped and allow the optimal development of usable leaves. For details on this subject, please refer to pages 233-262 of Principles of Flue-cured Tobacco Production by S. N. Hawks, Jr. and W. K. Collins, North Carolina State University (1983), and pages 71-81 of Plant Growth Regulating Chemicals, Vol. I, Ed. L. G. Nickel, CRC Press (1983).

In the chemical control of tobacco suckers, it is important that the chemical operates systemically; i.e., it should inhibit sucker development even when applied to other parts of the tobacco plant. This is important because in field-grown tobacco, the axillary buds, or suckers, are hidden in large leaf whorls. Thus, it is very difficult to apply the chemical spray such that it will directly contact the axillary buds. However, if the chemical operates systemically, this problem can be avoided because the chemical can be effectively applied to the leaves of the tobacco plant or even as a soil drench.

The most commonly used chemicals for tobacco sucker control are maleic hydrazide and flumetrain. Maleic hydrazide is a systemic inhibitor and though effective, it is not without its problems. Treatment with maleic hydrazide tends to leave undesirably high levels of residues in the leaves.

U.S. Pat. No. 4,440,566, issued April 3, 1984, discloses compounds having the formula:

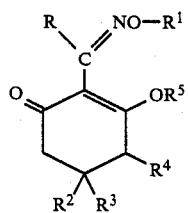

wherein

R is most preferably alkyl of 1 to 3 carbon atoms, most preferably ethyl or propyl;

$R^1$ is most preferably 3-trans-chloroallyl or 4-chlorobenzyl;

$R^2$ and $R^3$ are preferably each alkyl of 1 to 3 carbon atoms or one of $R^2$ or $R^3$ is hydrogen and the other is alkylthioalkyl having 2 through 8 carbon atoms, most preferably $R^2$ and $R^3$ are each methyl or one of $R^2$ or $R^3$ is hydrogen and the other is 2-ethylthiopropyl.

This patent teaches that these compounds exhibit herbicidal activity against grasses and are safe with respect to broadleaf crops and also may be employed to prevent or retard the growth of lateral buds in plants and to promote the thinning out of fruit in various fruit trees.

U.S. Pat. No. 4,624,696, issued November 25, 1986, discloses compounds having the formula:

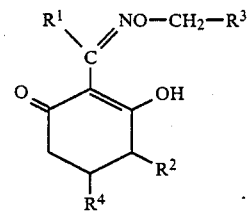

wherein $R^1$ is alkyl of 1 to 4 carbon atoms, $R^2$ is hydrogen or alkoxycarbonyl of 2 to 5 carbon atoms, $R^3$ is a 5-membered heterocyclic structure which contains 1 to 3 heteroatoms from the group consisting of N, O, and S and may contain 1 or 2 double bonds and 1 or 2 substituents from the group consisting of $C_1$-$C_4$-alkyl, $C_1$-$C_4$-alkoxy, halogen, trifluoromethyl, $C_1$-$C_4$-alkoxymethyl, $C_1$-$C_4$-alkylthiomethyl, vinyl and phenyl, and $R^4$ is a 5-membered to 7-membered heterocyclic structure which contains one heteroatom or ring member, or two identical or different heteroatoms or ring members, from the group consisting of N, O, S, SO, and $SO_2$, may contain 1, 2, or 3 double bonds and is unsubstituted or substituted by not more than 2 alkyl or alkoxy groups, each of 1 to 4 carbon atoms, or is a radical of the Formula II

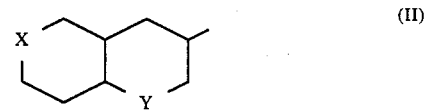

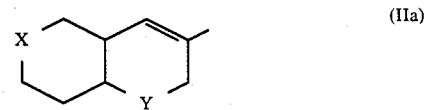

where X and Y are each N, O, S, SO, or $SO_2$, and salts of these compounds.

This patent teaches that $R^1$ is preferably a radical having two or three carbon atoms. The patent describes the compounds as exhibiting herbicidal activity against grasses and safe with respect to a number of enumerated crops.

The patent also teaches that these compounds exhibit herbicidal activity against grasses and are safe with respect to a number of crops.

U.S. Pat. No. 4,596,877 discloses compounds having the formula

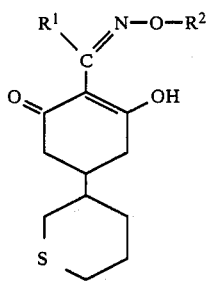

wherein $R^1$ is $C_1$–$C_4$ alkyl and $R^2$ is $C_3$–$C_5$ chloroalkenyl. $R^1$ is preferably ethyl or propyl.

The compounds are described as being effective to remove grasses while being safe for a number of crops.

U.S. Pat. No. 4,432,786 discloses compounds having the following formula and their salts:

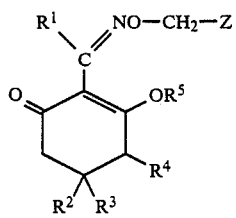

wherein $R^1$ is hydrogen or lower alkyl;

$R^2$ and $R^3$ are independently selected from the group consisting of hydrogen, lower alkyl, aryl having 6 through 10 carbon atoms (preferably phenyl), substituted aryl having 6 through 10 carbon atoms (preferably phenyl) and 1 through 4 substituents (preferably 1 or 2) independently selected from the group consisting of fluoro, chloro, bromo, iodo, or trifluoromethyl;

$R^4$ is hydrogen or alkoxycarbonyl having 2 through 4 carbon atoms;

$R^5$ is hydrogen, or an acyl group having 1 through 12 carbon atoms; and

Z is a group having the formula:

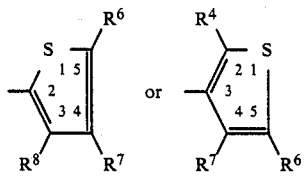

wherein $R^6$, $R^7$, and $R^8$ are independently selected from the group of hydrogen, halo, nitro, alkyl having 1 through 4 carbon atoms, alkoxy having 1 through 4 carbon atoms, or trifluoromethyl.

The compounds wherein $R^1$ is ethyl or propyl and/or Z is a chlorothienyl are preferred. The compounds are described as exhibiting excellent grass herbicidal activity.

Certain 2-acyl-3-hydroxy-5-heterocyclecyclohexenone derivatives are described in German application DE No. 3,522,213 laid open January 2, 1987, as exhibiting a variety of plant growth regulating activities including preventing suckering in tobacco.

Commonly assigned U.S. application Ser. No. 854,448 filed Apr. 21, 1986, non U.S. Pat. No. 4,701,205 discloses that certain 2-[1-(3-chloroallyloxyimino)e- thyl]-3-hydroxy-5-(2-substituted thioalkylidene)-cyclohex-2-en-1-one derivatives are useful to control tobacco suckers.

SUMMARY OF THE INVENTION

It has now been discovered that certain 3-hydroxy-cyclohex-2-en-1-ones and 3-alkanoyl esters thereof exhibit a surprising superior ability to control (inhibit) tobacco sucker growth. This activity is surprising and does not appear to exist throughout the class of 3-hydroxy and esterified 3-alkanoyl derivatives of 2-[1-(substituted-oxyimino)alkyl]-3-hydroxy-5-substituted-cyclohex-2-en-1-ones as a whole. At moderate dosage rate, the 3-alkanoyl ester derivatives also inhibit the growth of secondary sucker growth as well as primary sucker growth. These compounds are further readily absorbed and translocated within the tobacco plant so that the compounds do not have to directly contact the axillary buds to be effective. As discussed above, this affords a substantial advantage in applying the material.

Thus, in one aspect the invention provides a process for inhibiting the growth of axillary buds tobacco plants which comprises applying to said tobacco plants or their growth medium an amount effective to inhibit the growth of said axillary buds of a growth control agent selected from the group of compounds having the formula:

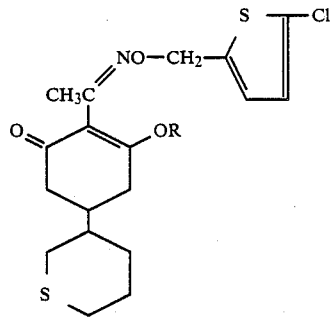

wherein R is hydrogen or the

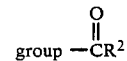

group $-CR^2$ wherein $R^2$ is alkyl having 1 through 10 carbon atoms, preferably 1 through 7 carbon atoms;
and mixtures of compounds according to Formula I.

The use of the compatible salts of the compounds of Formula I wherein R is hydrogen are also encompassed within the invention.

As is well recognized, compounds of the nature of Formula (I) exist as tautomers. The compounds also have two or more asymmetric carbon atoms and thus can also exist as optical isomers. The above formula is intended to encompass the respective tautomeric forms as well as the individual optical isomers as well as mixtures thereof and the respective tautomers and optical isomers as well as mixtures thereof are encompassed within the invention.

In a further aspect the invention provides a tobacco axillary bud controlling composition comprising a compatible carrier and a tobacco axillary bud controlling effective amount of the compound(s) of Formula I or mixtures thereof.

The invention will be further described hereinbelow.

FURTHER DESCRIPTION OF THE INVENTION AND THE PREFERRED EMBODIMENTS

In general the compounds where R is alkanoyl

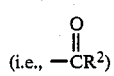

(i.e., $-\overset{O}{\underset{\|}{C}}R^2$)

are more effective for controlling tobacco suckers than the corresponding 3-hydroxy compound (i.e., R is hydrogen) or its salts, though both are highly active for this purpose.

The preferred compounds for controlling tobacco suckers (i.e., axillary buds) are those wherein $R_2$ is alkyl having 1 to 7 carbon atoms, more preferably 1 to 3 carbon atoms and most preferably methyl, ethyl, or n-propyl.

Typically, the compounds are applied at application rates of 0.1-3.2 kilograms per hectare ("Kg/ha") preferably 0.4-2 Kg/ha. Best results are typically obtained using application rates of about from 0.8-1.6 Kg/ha. Mixtures of the compounds of Formula I can also be used. Optimum results may vary with the particular compound or compounds of Formula I used and the particular species of tobacco but can be obtained by routine experimentation. At high dosage rates (e.g., 5 kg/ha or above) certain of the compounds exhibit phytotoxicity with respect to certain broadleaf plants as well as grasses. Thus, high dosage rates should be avoided.

As noted above, it is conventional to remove the terminal growing meristem of the tobacco plant in order to optimize the number and quality of usable leaves. In accordance, with the practice of the present invention, it is preferable to apply the compounds of Formula I or their salts within two days, more preferably a day after removal of the terminal growing meristem. The compounds can be applied directly to the plants or to the soil. Most typically the compound is applied as a solution or liquid emulsion.

Although in theory the compounds can be applied undiluted, in actual practice they are generally applied as a composition or formulation, comprising an effective amount of the compound(s) of Formula I or their salts and an acceptable carrier. An acceptable or compatible carrier (agriculturally acceptable carrier) is one which does not significantly adversely affect the desired biological effect achieved by the active compounds, save to dilute it. The compositions can be prepared, both for direct application and also a concentrate designed for dilution prior to application. The carrier can be a solid, liquid, or aerosol. The actual compositions can take the form of granules, powders, dusts, solutions, emulsions, slurries, aerosols, and the like.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seed hulls, wheat flour, wood flour, wood bark flour, and the like can also be used as carriers. Suitable liquid diluents or carriers which can be used include, for example, water, organic solvents (e.g., hydrocarbons such as benzene, toluene, dimethylsulfoxide, kerosene, diesel fuel, fuel oil, petroleum naphtha, etc.), and the like. Suitable aerosol carriers which can be used include conventional aerosol carriers such as halogenated alkanes, etc.

The composition can also contain various promoters and surface-active agents which enhance the rate of transport of the active compound into the plant tissue such as, for example, organic solvents, wetting agents and oils.

The composition can also contain various compatible adjuvants, stabilizers, conditioners, insecticides, fungicides.

One convenient concentrate formulation which can be used comprises 20-30 by weight percent of the compound(s) of Formula I or salts thereof, of the invention, 2-4 by weight percent of an emulsifier, for example, alkylarylsulfonates, e.g., calcium alkylbenzene sulfonates, octylphenolethoxylate, polyoxyethylenealkylaryl, etc., or mixtures thereof, and about 66-76% organic solvent, for example, petroleum hydrocarbon and aromatics, e.g., xylene, kerosene, etc. For example, one suitable concentrate formulation which can be used comprises about 25 wt % of the active compound; about 72 wt % of a xylene base solvent sold under the Trademark "HiSol 10" by Ashland Oil Company, as the solvent and about 3 wt % of mixture of alkylarylsulfonates and polyoxyethylenealkylaryl sold under the Trademark "Atlox 3454F" as the emulsifier.

The concentrate can be mixed with water, optionally containing a crop oil, prior to application and applied as a water emulsion, optionally containing about 0.125-2 wt % of a crop oil, for example, soybean oils, and paraffinic oils and olefinic oils and/or surfactant. Conveniently, the composition is applied as a water emulsion spray containing about 0.01-0.32 wt %, preferably 0.04-0.16 wt % of the compound(s) of Formula I or salts thereof; about 0.001-0.0625 wt % of an emulsifier; about 0.08-3.3 wt % of an organic solvent and about 95-99 wt % water and optionally 0.125-2 wt % crop oil. The spray composition can be conveniently prepared by mixing the concentrate formulation with about ¼-½ the desired amount of water. Then admixing the crop oil, if used, and then adding the remaining amount of water. If no crop oil or additional surfactant is used, then the water and concentrate formulation are simply admixed together.

The compound of Formula I can be conveniently prepared by the procedures described in commonly assigned copending application Ser. No. 101,321, filed on even date herewith. For example:

The compound of Formula I can be conveniently prepared by the following schematically represented process:

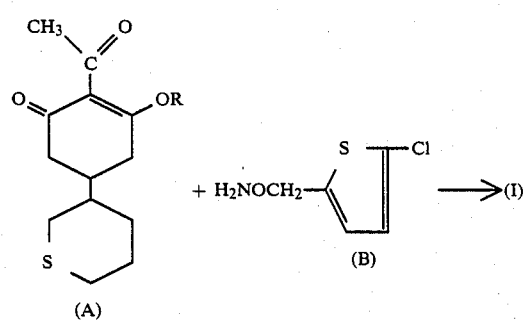

wherein R is as defined hereinabove.

This process can be conveniently effected by contacting Compound (A) with (5-chlorothien-2-yl)methoxyamine (B), under reactive conditions preferably in an inert organic solvent.

Typically, this process is conducted at temperatures in the range of about from 0°–80° C., preferably about from 20°–40° C., for about from 1–48 hours, preferably about from 4–12 hours, using about from 1–2, preferably 1.05–1.2 moles of (5-chlorothien-2-yl)methoxyamine (B) per mole of Compound (A). Suitable inert organic solvents which can be used include, for example, lower alkanols, e.g., methanol, ethanol; ethers, e.g., ethyl ether; methylene chloride. Two-phase water and immiscible organic solvent (e.g., hexane), and mixtures thereof can also be used as the reaction medium.

(5-chlorothien-2-yl)methoxyamine is a known compound and can be prepared via known procedures, such as, for example, described U.S. Pat. No. 4,432,786. The (5-chlorothien-2-yl)methoxyamine reactant can be conveniently provided by neutralizing its hydrochloride salt in situ with an alkali metal alkoxide.

The compound of Formula A wherein R is alkanaly can be conveniently prepared by acylating the corresponding 3-hydroxy compound:

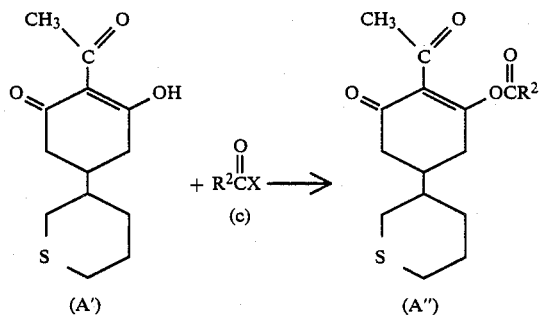

wherein R² is as defined hereinabove.

This process can be effected by contacting Compound A' with the appropriate acyl halide under reactive conditions preferably in an inert organic solvent and preferably in the presence of a scavenger base.

Typically this process is conducted at temperatures in the range of about from −78° to 100° C., preferably 0° to 25° C. for about from 1 to 48 hours using about from 1 to 5 moles, preferably 1 to 1.2 moles of acyl halide (c) per mole of Compound A'. Where a scavenger base is used typically about from 1 to 5, preferably 1 to 1.2 moles of scavenger base is used per mole of Compound A'. Suitable scavenger bases which can be used include, for example, triethylamine, pyridine, methylpyridine, 2,4-lutidine, and the like. Suitable solvents which can be used include, for example methylene chloride, chloroform, ethyl acetate, acetonitrile, diethyl ether, tetrahydrofuran, and the like.

The R is alkanoyl compounds of Formula I can also be prepared by acylating the 3-hydroxy analog of Formula I wherein R is hydrogen. For example, the acylation can be effected using the appropriate acyl halide using substantially the same conditions as described above with respect to the acylation of Compound A'. Other acylating agents could also be used in either case such as, for example, acyl anhydrides. The compounds of Formula A' and the 3-hydroxy compound of Formula I can be prepared via the procedure described in U.S. Pat. No. 4,624,696.

The compatible salts of the compounds of Formula (I) can be prepared by conventional procedures, for example, via the reaction of the compound of Formula I, wherein R is hydrogen, with a base, such as, for example, sodium hydroxide, potassium hydroxide and the like, having the desired cation. Additional variations in the salt cation can also be effected via ion exchange with an ion exchange resin having the desired cation.

The term "compatible salts" refers to salts which do not significantly adversely alter the herbicidal properties of the parent compound. Suitable salts include cation salts such as, for example, the cation salts of lithium, sodium, potassium, alkali earth metals, copper, zinc, ammonia, quaternary ammonium salts, and the like.

General Process Conditions

The reaction product can be recovered from its reaction product mixture by any suitable separation and purification procedure, such as, for example, chromatography. Suitable separation and purification procedures are, for example, illustrated in the Examples set forth hereinbelow.

Generally, the reactions described above are conducted as liquid phase reaction and hence pressure is generally not significant except as it affects temperature (boiling point) where reactions are conducted at reflux. Therefore, these reactions are generally conducted at pressures of about from 300–3000 mm of mercury and conveniently are conducted at about atmospheric or ambient pressure.

It should also be appreciated that where typical or preferred process conditions (e.g., reaction temperatures, times, mole ratios of reactants, solvents, etc.) have been given, that other process conditions could also be used. Optimum reaction conditions (e.g., temperature, reaction time, mol ratios, solvents, etc.) may vary with the particular reagents or organic solvents used but can be determined by routine optimization procedures.

Definitions

As used herein the following terms have the following meanings unless expressly stated to the contrary:

The term "alkyl" includes both straight chain and branched chain alkyl groups.

The term "alkylidene" includes both straight chain and branched chain alkylidene groups and includes, for example, groups having the formula

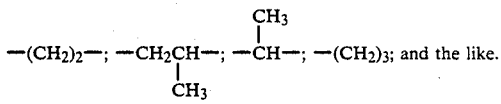

The term "room temperature" or "ambient temperature" refers to about 20°–25° C.

A further understanding of the invention can be had in the following non-limiting Preparation(s) and Example(s). Wherein, unless expressly stated to the contrary, all temperatures and temperature ranges refer to the Centigrade system and the term "ambient" or "room temperature" refers to about 20°–25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume.

EXAMPLES

Example 1

3-Acetyloxy-2-[1-[(5-chlorothien-2-yl)methoxyimino]ethyl]-5-(tetrahydro-2H-thiopyran-3-yl)-cyclohex-2-en-1-one In this example, 0.52 g (5.1 mmol) of triethylamine was admixed to a solution containing 1.46 g (3.7 mmol) of 2-[1-[(5-chlorothien-2-yl)methoxyimino]ethyl]-3-hydroxy-5-(tetrahydro-2H-thiopyran-3-yl)-cyclohex-2-en-1-one in 30 ml of methylene chloride at room temperature (about 20°–25° C.) followed by the dropwise addition of 0.35 g (4.4 mmol) of acetyl chloride. The mixture was stirred at room temperature overnight (about 14 hr) and then washed with saturated aqueous sodium bicarbonate solution, followed by saturated sodium chloride solution. The washed extract was dried over anhydrous magnesium sulfate and concentrated under reduced pressure. The product was purified by column chromatography on silica gel to afford 1.0 g of the title compound as a pale yellow oil; IR (neat) 1775 $cm^{-1}$; $^1H$ NMR spectrum (90 MHz $CDCl_3$) $\epsilon$ 1.00–2.60 (m, 14H), 1.93 (s, 3H), 2.00 (s, 3H), 5.07 (s, 2H) 6.73 (s, 2H).

Similarly, by applying the above procedure using the appropriate acyl chloride the following compounds can be prepared:

3-propionyloxy-2-[1-[(5-chlorothien-2-yl)methoxyimino]ethyl]-5-(tetrahydro-2H-thiopyran-3-yl)cyclohex-2-en-1-one;

3-butyryloxy-2-[1-[(5-chlorothien-2yl)methoxyimino]ethyl]-5-(tetrahydro-2H-thiopyran-3-yl)-cyclohex-2-en-1-one;

3-isobutyryloxy-2-[1-(5-chlorothien-2yl)methoxyimino]ethyl]-5-(tetrahydro-2H-thiopyran-3-yl)-cyclohex-2-en-1-one;

3-valeryloxy-2-[1-[(5-chlorothien-2yl)methoxyimino]ethyl]-5-(tetrahydro-2H-thiopyran-3-yl)cyclohex-2-en-1-one;

3-isovaleryloxy-2-[1-[(5-chlorothien-2yl)methoxyimino]ethyl]-5-(tetrahydro-2H-thiopyran-3-yl)cyclohex-2-en-1-one;

3-pivaloyloxy-2-[1-[(5-chlorothien-2yl)methoxyimino]ethyl]-5-(tetrahydro-2H-thiopyran-3-yl)cyclohex-2-en-1-one;

3-hexanoyloxy-2-[1-[(5-chlorothien-2yl)methoxyimino]ethyl]-5-(tetrahydro-2H-thiopyran-3-yl)cyclohex-2-en-1-one;

3-heptanoyloxy-2-[1-[(5-chlorothien-2yl)methoxyimino]ethyl]-5-(tetrahydro-2H-thiopyran-3-yl)cyclohex-2-en-1-one; and 3-(2-ethylhexanoyloxy-2-[1-[(5-chlorothien-2yl)methoxyimino]ethyl]-5-(tetrahydro-2H-thiopyran-3-yl)cyclohex-2-en-1-one.

EXAMPLE 2

3-Acetyloxy-2-[1-[(5-chlorothien-2-yl)methoxyimino]ethyl]-5-(tetrahydro-2H-thiopyran-3-yl)-cyclohex-2-en-1-one The title compound can be prepared by the following procedure:

0.34 g (2.0 mmol) of (5-chlorothien-2-yl)methoxyamine is added to a stirred solution of 0.59 g (2.0 mmol) of 2-acetyl-3-acetyloxy-5-(tetrahydro-2H-thiopyran-3-yl)cyclohex-2-en-1-one in 10 ml of absolute ethanol. After stirring overnight at room temperature, the reaction mixture is concentrated under reduced pressure. The resulting residue is diluted with 25 ml of dichloromethane and washed twice with 10 ml of saturated sodium chloride solution. The washed extract is then dried over anhydrous magnesium sulfate and evaporated under reduced pressure. The product can then be purified by column chromatography employing tetrahydrofuran-hexane (1:2 by volume) as eluent to afford the title compound.

EXAMPLE 3

In this example, the compounds identified in Table A hereinbelow were tested for their ability to control (retard or prevent) lateral axillary buds in tobacco plants.

These tests were conducted using the following procedure.

The results are reported as an average of the replicates used in each test. The results of these tests and the dosage rates, evaluation times, etc., used are indicated in the following tables.

The tobacco plants used in these studies were topped approximately 2 hours before chemical treatment. Topping was done by removing all but 8 fully expanded leaves. Any plants that showed premature yellowing of leaves or bending of stems were discarded. All the pots were labeled and 5 replicates were used for each treatment.

A stock solution was prepared by dissolving the respective compound in acetone containing a non-ionic emulsifier. The stock solution was diluted with deionized water containing 0.625 g of emulsifier per liter of water, to the desired spray solution concentrations. The exact concentration and species of tobacco plant used for testing are indicated in the individual data charts.

Each treatment was applied until run-off to individual plants with a pressure atomizer to ensure good coverage of various plant parts with the chemical solution. The only exception to this rule was the experiment on translocation studies (Test No. 13439) where the compound was either painted on the leaf with a fine paint brush or applied as a solil drench treatment. Each plant was sprayed with 7–10 ml of solution. After spraying, the plants were maintained in a greenhouse at 70°–80° F. for up to 6 weeks depending on the experiment. All plants were fertilized once a week with a standard garden fertilizer. Readings were taken on percent sucker control at different time intervals. This was accomplished by making visual assessment of bud growth in treated plants compared to bud growth in untreated plants, also referred to as checks. Data was recorded as percent bud inhibition (sucker control), with 0=no inhibition of buds and 100=total inhibition buds, compared to untreated checks. The sucker development of the top 3 nodes was referred to as primary suckers whereas the sucker development on lower nodes was referred to as secondary suckers. (In general, primary suckers are substantially more detrimental to tobacco production than secondary suckers.)

TABLE A

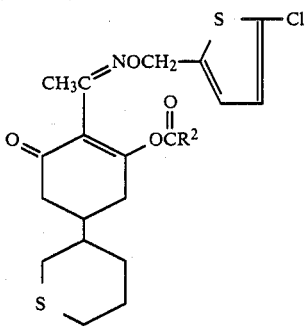

| Compound No. | R² |
|---|---|
| 1 | CH₃ |
| 2 | CH₃CH₂— |
| 3 | CH₃(CH₂)₂— |
| 4 | CH₃(CH₂)₃— |
| 5 | CH₃(CH₂)₄— |

TABLE 1

Tobacco Sucker Control (Var. Glurk)[1]
Three Weeks After Treatment[3]

| Compound | Dosage[2] Concentration mg/l | Percent Primary Sucker Inhibition |
|---|---|---|
| 1 | 100 | 93 |
| 1 | 50 | 80 |
| 1 | 25 | 30 |
| 1 | 12.5 | 0 |
| 2 | 100 | 91 |
| 2 | 50 | 73 |
| 2 | 25 | 33 |
| 2 | 12.5 | 0 |
| 3 | 100 | 98 |
| 3 | 50 | 85 |
| 3 | 25 | 20 |
| 3 | 12.5 | 0 |
| 4 | 100 | 94 |
| 4 | 50 | 58 |
| 4 | 25 | 28 |
| 4 | 12.5 | 0 |
| 5 | 100 | 97 |
| 5 | 50 | 71 |
| 5 | 25 | 0 |
| 5 | 12.5 | 0 |

| Compound | Six Weeks After Treatment[3] Dosage[2] Concentration mg/l | Percent Primary Sucker Inhibition Top two Nodes | Number of Secondary Suckers[4] |
|---|---|---|---|
| 1 | 200 | 99 | 0.2 |
| 1 | 100 | 99 | 2.5 |
| 1 | 50 | 98 | 5.2 |
| 1 | 25 | 98 | 6.0 |
| 2 | 100 | 50 | 1.5 |
| 2 | 50 | 35 | 1.5 |
| 2 | 25 | 28 | 1.3 |
| 2 | 12.5 | 8 | 3.0 |
| 3 | 100 | 80 | 5.5 |
| 3 | 50 | 40 | 1.8 |
| 3 | 25 | 20 | 1.0 |
| 3 | 12.5 | 5 | 2.3 |
| 4 | 100 | 61 | 1.5 |
| 4 | 50 | 35 | 0.8 |
| 4 | 25 | 23 | 1.0 |
| 4 | 12.5 | 3 | 1.8 |
| 5 | 100 | 78 | 2.8 |
| 5 | 50 | 25 | 0.5 |
| 5 | 25 | 0 | 0.8 |
| 5 | 12.5 | 0 | 2.0 |

[1]Var. Glurk: Nicotiana tabacum (At the spray volume and area used in the tests 1000 mg/l equals an application rate approximately 1 Kg/ha)
[2]Concentration of test compound in spray solution
[3]Weeks after spraying of tobacco plants with test compound
[4]i.e., Axillary buds at lower nodes

EXAMPLE 4

In this example, the Compound No. 1 was tested side-by-side with its 3-hydroxy analog (Compound No. 6) for tobacco sucker control. These tests were conducted following the same general procedure as described in Example 3 hereinabove using the dosage concentrations given in the tables hereinbelow.

TABLE 2

Tobacco Sucker Control (Var. Glurk)[1]
Three Weeks After Treatment[3]

| Compound | Dosage[2] Concentration mg/l | Percent Bud Inhibition Primary Suckers Var. Glurk[1] |
|---|---|---|
| 1[4] | 200 | 100 |
| 1 | 100 | 100 |
| 1 | 50 | 99 |
| 1 | 25 | 92 |
| 6[4] | 200 | 100 |
| 6 | 100 | 100 |
| 6 | 50 | 100 |
| 6 | 25 | 38 |
| Check | — | 0 |

[1]Variety Glurk: Nicotiana tabacum
[2]Concentration of test compound in spray solution; at volume and area used, 1000 mg/l equals about 1 Kg/ha
[3]Weeks after spraying of tobacco plants with test compound
[4]Compound No. 6 is 3-hydroxy-2-[1-(5-chlorothien-2-ylmethoxyimino)ethyl]-5-(tetrahydro-2H-thiopyran-3-yl)-cyclohex-2-en-1-one As can be seen from the above test, both compounds exhibited excellent sucker control at high to moderate dosage rates, but at the low 25 mg/l application rate Compound 6 exhibited only poor (i.e., 38%) sucker control whereas Compound 1 still exhibited very good sucker control (i.e., 92%).

EXAMPLE 5

2-[1-[(5-chlorothien-2-yl)methoxyimino]ethyl]-3-hydroxy-5-(tetrahydro-2H-thiopyran-3-yl)cyclohex-2-en-1-one A solution containing 5.1 g (0.020 mol) of 2-acetyl-3-hydroxy-5-(tetrahydro-2H-thiopyran-3-yl)cyclohex-2-en-1-one and 3.4 g (0.021 mol) of (5-chlorothien-2-yl)methoxyamine in 200 ml of ethanol was stirred overnight (about 14 hours) at room temprature and then evaporated to remove ethanol. The concentrate was diluted with 150 ml of methylene chloride and then washed with 100 ml of water and then with 100 ml of saturated aqueous sodium chloride solution. The washed methylene chloride solution was dried over anhydrous magnesium sulfate and then evaporated to dryness under reduced pressure to afford a white solid. Recrystallation of this solid absolute ethanol afforded 7.6 g of the title compound, m.p. 154°–155° C.

EXAMPLE 6

Sodium 2-[1-[(5-chlorothien-2-yl)methoxyimino]ethyl]-3-oxo-5-(tetrahydro-2H-thiopyran-3-yl)-cyclohex-1-en-1-olate This example illustrates a procedure which can be used to prepare the title compound.

A solution containing 0.01 mol of sodium hydroxide dissolved in 2 ml of water is added to a solution containing 0.01 mol of 2-[1-[(5-chlorothien-2-yl)methoxyimino]ethyl]-3-hydroxy-5-(tetrahydro-2H-thiopyran-3-yl)-cyclohex-2-en-1-one at room temperature. After the reaction is completed, the solvents are evaporated off under vacuum affording the 1-hydroxy sodium salt of 2-[1-[(5-chlorothien-2-yl)methoxyimino]ethyl]-3-hydroxy-5-(tetrahydro-2H-thiopyran-3-yl)-cyclohex-2-en-1-one.

Obviously, many modifications and variations of the invention described hereinabove and below can be made without departing from the essence and scope thereof.

What is claimed is:

1. A method for inhibiting the growth of axillary buds in tobacco plants which comprises applying to said tobacco plants or their growth medium an amount effective to inhibit the growth of axillary buds of a growth control agent selected from the group of compounds having the formula:

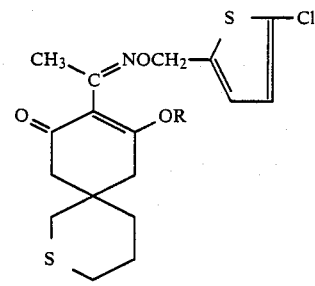

wherein

R is hydrogen or the group —C(O)R$^2$ wherein R$^2$ is alkyl having 1 through 6 carbon atoms; and compatible salts thereof; and mixtures thereof.

2. The method of claim 1 wherein R is —C(O)R$^2$ wherein R$^2$ is alkyl having 1 through 3 carbon atoms.

3. The method of claim 2 wherein R$^2$ is methyl, ethyl or n-propyl.

4. The method of claim 3 wherein R$^2$ is methyl.

5. The method of claim 1 wherein R is hydrogen.

6. The method of claim 1 wherein said growth control agent is applied at a rate of about from 0.4–2 kg/ha.

7. The method of claim 3 wherein said growth control agent is applied at a rate of about from 0.4–2 kg/ha.

* * * * *